United States Patent [19]

Cooper

[11] Patent Number: 4,568,336
[45] Date of Patent: Feb. 4, 1986

[54] PRE-FILLED HYPODERMIC SYRINGES
[75] Inventor: Murray S. Cooper, Islamorada, Fla.
[73] Assignee: Microbiological Applications, Inc., Islamorada, Fla.
[21] Appl. No.: 604,006
[22] Filed: Apr. 26, 1984
[51] Int. Cl.⁴ .............................................. A61M 5/00
[52] U.S. Cl. .................... 604/240; 604/201; 604/232; 604/243; 604/244; 604/242; 604/413; 604/905
[58] Field of Search ............... 604/240, 201, 202, 232, 604/238, 243, 244, 272, 413–415, 505

[56] References Cited
U.S. PATENT DOCUMENTS

| 2,545,017 | 3/1951 | Billingsley | 604/143 |
|---|---|---|---|
| 2,629,379 | 2/1953 | Fields | 604/415 |
| 2,706,984 | 4/1955 | Lipari | 604/232 |
| 2,842,126 | 7/1958 | Brown | 604/201 |
| 2,874,694 | 2/1959 | Blackman | 604/232 |
| 2,922,419 | 1/1960 | Bednarz | 604/201 |
| 3,375,825 | 4/1968 | Keller | 604/201 |
| 3,387,609 | 6/1968 | Shields | 604/202 |
| 3,542,240 | 11/1970 | Solowey | 604/415 |
| 4,203,443 | 5/1980 | Genese | 604/413 |
| 4,334,536 | 6/1982 | Pfleger | 604/201 |

Primary Examiner—C. Fred Rosenbaum
Assistant Examiner—Mark Rooney
Attorney, Agent, or Firm—Leon E. Tenenbaum

[57] ABSTRACT

A hypodermic syringe capable of pre-filling aseptically from either end. Both ends of the rimmed syringe barrel are sealed and capped with standard vaccine or syringe vial closures and crimped aluminum seals. Both ends of the pre-filled and sealed syringe maintain assured sterility integrity by guaranteed microbe-proof barriers during the entire shelf life of package or container. The syringe is prepared for use by simply removing protective caps or seals. The needle assembly is packaged separately and placed in position on syringe by a simple action.

2 Claims, 5 Drawing Figures

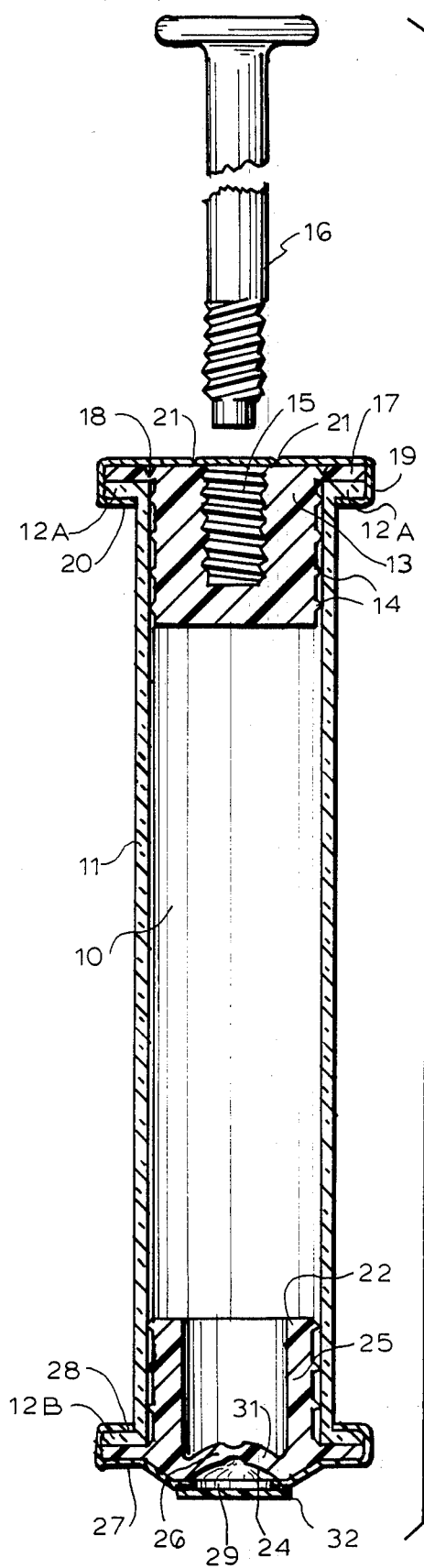
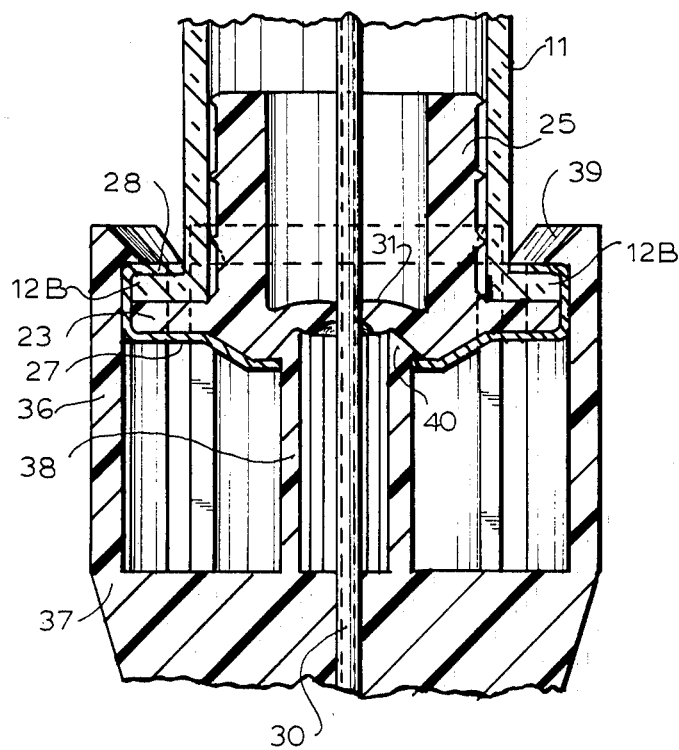
FIG. 1
FIG. 5

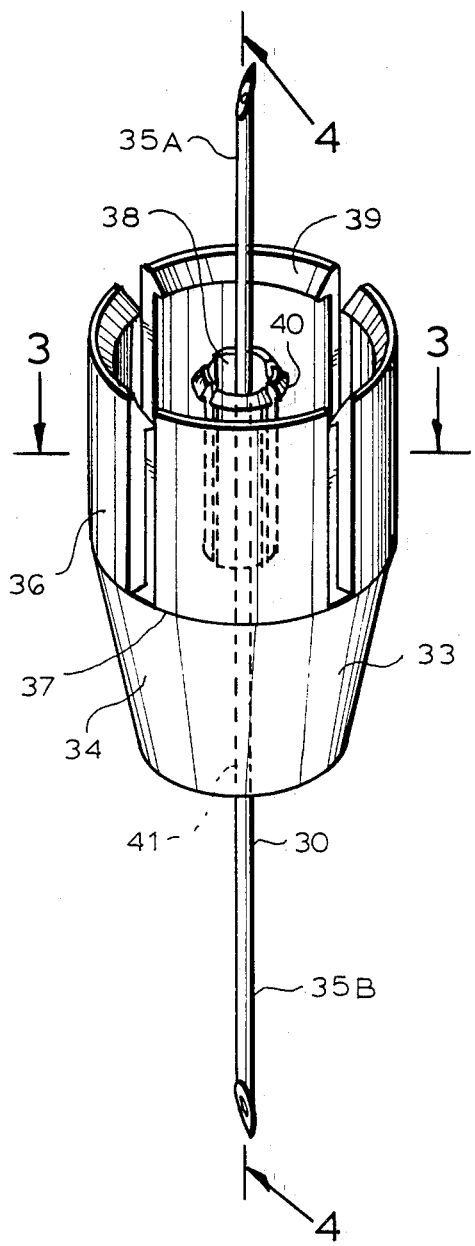
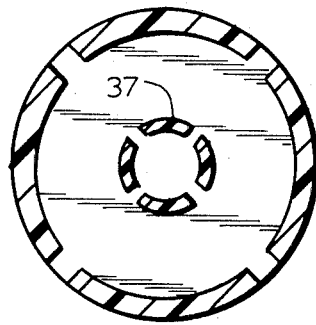
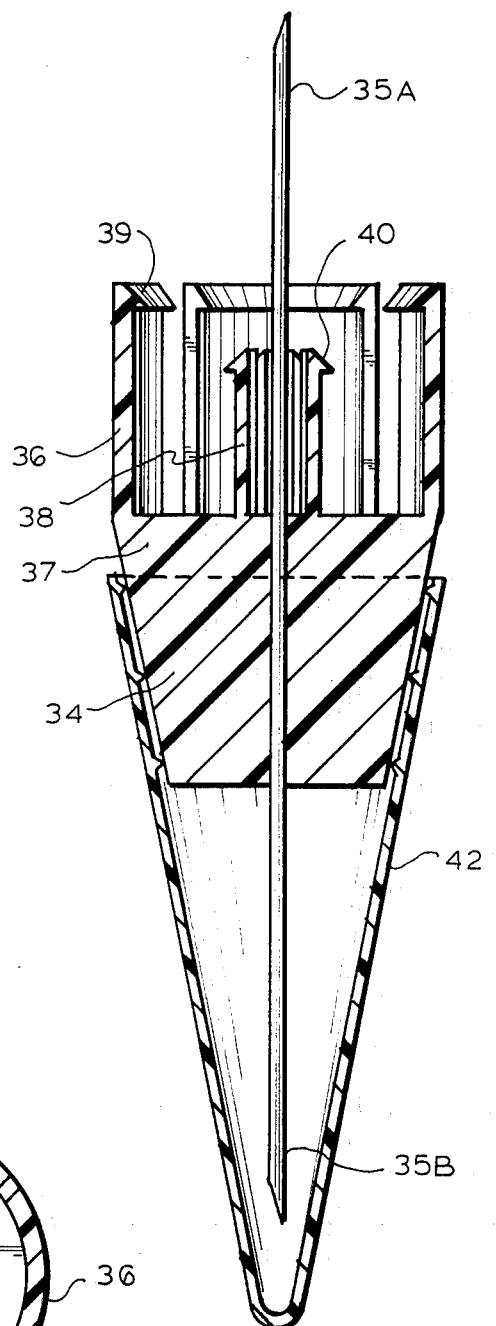
FIG. 2
FIG. 3
FIG. 4

PRE-FILLED HYPODERMIC SYRINGES

This invention relates to pre-filled hypodermic syringes. It particularly relates to disposable pre-filled hypodermic syringes of improved sterility integrity.

BACKGROUND OF THE INVENTION

Prefilled hypodermic syringes containing medicaments purporting to be sterile are an important means of delivering safe single dose medicaments to the point of administration. The volume of products prepared in this manner is continuallly increasing due to the advantages of this delivery system.

However, in view of the structural complexities of this type of syringe, there are many problems involved in the fabrication of a prefilled syringe container which assures the sterility of the contents, is economically practicable, and is convenient to use. In particular, the sterility problems associated with these prefilled hypodermic syringes have been recognized by both governmental agencies (e.g. FDA) and industrial associations (e.g. Parenteral Drug Association), and various guidelines and procedures have been provided for assuring the sterility of these products. These procedures are costly and difficult to carry out. The sterility problems come from three (3) sources, (i) initial sterilization, (ii) aseptic filling and sealing and (iii) maintenance of sterility during the normal shelf life of the product.

It is difficult, due to the nature of the hypodermic syringe now in use, to design one which can be effectively sterilized prior to aseptically filling with the required sterile medicament. The aseptic filling and sealing operation is also more difficult to accomplish with a hypodermic syringe container rather than the standard serum vial or ampule which is currently employed for packaging injectible pharmaceuticals purporting to be sterile. The added complex procedures necessary to prefill a hypodermic syringe result in a greater possibility of contamination and the consequent presence of nonsterile units in the filling lot.

Another problem with the currently available prefilled hypodermic syringes is the limited or questionable sterility integrity of the container during the expected shelf life of the product. This limitation is due primarily to the typical design of the closure and sealing systems employed.

Many approaches have been tried to meet this problem of sterility. In the hypodermic syringes disclosed in U.S. Pat. Nos. 4,314,556; 4,317,446; 4,281,653 and 4,235,235, the elastomeric closure which also serves as the piston or plunger is placed entirely inside the prefilled syringe barrel or cylinder. The assurance of continuing sterility therefore is limited only to the pressure of the one or more annular rings on the rim of the elastomeric piston or plunger. Since the elastomeric piston or plunger must ultimately be depressed in the syringe cylinder in order to express the injection dose, the fit of the piston cannot of necessity be extremely tight, since if it were, it would hinder the movement of the piston or plunger.

Sometimes lubricants have been employed to ease the movement of the plunger. Usually, the plunger and the syringe barrel are coated with a medical grade silicone. However, the amount of the lubricant being used must be carefully controlled since at times these lubricants may end up as globules in the liquid medicament and this can be very dangerous to the patient receiving the injection.

Another limitation in the design of some of the currently marketed prefilled syringes is the needle assembly. In these units where the needle assembly is permanently affixed to the syringe barrel, a special shield and closure for the needle is necessary in order to prevent the contained medicament liquid from leaking out of the syringe barrel through the needle. In order to accomplish this the point of the needle is actually imbedded into an elastomeric shield. This sealing procedure must obviously be completed prior to the aseptic filling of the barrel with the sterile medicament. The sterilization of the empty syringe including the imbedded needle is usually accomplished by employment of steam or ethylene oxide gas. The limitations of this sterilization procedure are due to the nature of the seal employed with the needle assembly. The imbedding of the needle tip into the elastomeric shield results in a section of the needle being insulated from the sterilization process. This defect is shown in U.S. Pat. No. 4,317,446 and in many widely distributed prefilled hypodermic syringes now on the market.

THE PRESENT INVENTION

It is an object of this invention to provide a prefilled hypodermic syringe of high sterility integrity.

It is another object of this invention to provide a pre-filled hypodermic syringe in which the barrel portion containing the medicament can be filled from either end, the filling operation being as simple as in the filling of a serum vial or ampule.

It is still another object of this invention to provide a closed sterile unit containing a sterile solution of a medicament, said unit being adapted for use in a hypodermic syringe.

It is a further object of this invention to provide a pre-filled hypodermic syringe in which one of the closure means for said barrel portion is the piston and the other closure means is adapted to receive a needle.

Other objects will appear from the description which follows.

In accordance with this invention there is provided a hypodermic syringe comprised of a tubular syringe body adapted to be filled at either end, piston closure means at one end of said syringe body, said closure means being adapted to receive an activating rod, closure means at the opposite end of said syringe body, said closure means being adapted to receive a needle and holding means for said needle, said holding means being adapted to be secured to the closure means for receiving the needle.

The invenion will be clearer from the drawings and description which follow. These drawings and the embodiments described in connection therewith are only given by way of illustration and are not to be considered as limiting.

DRAWING AND DESCRIPTION OF EMBODIMENTS

Referring to the drawings:

FIG. 1 is a longitudinal sectional view through the entire length of the tubular barrel portion of the syringe with the covers in place on both ends of the tubular barrel.

FIG. 2 is a perspective view of the holder of the needle with the needle in place.

FIG. 3 is a sectional view along the line 3—3 of FIG. 2.

FIG. 4 is a sectional view along the line 4—4 of FIG. 2.

FIG. 5 is a fragmentary section of the holder and needle joined to the syringe.

Referring now to the drawing the unit 10 for holding the medicament solution is comprised of a tubular syringe body 11 which can be filled at either end. The tubular body is provided with outwardly projecting circular flanges 12A and 12B at each end. The tube may be fabricated from glass or any suitable, preferably clear, hard plastic which is inert to the medicament solution. One end of said tubular body is provided with elastomeric piston closure means comprising of a plunger 13, said plunger being provided with substantially evenly spaced annular rings 14, integral with the closure, which fit snugly against the inner wall of the tube, a receptacle 15, preferably threaded, for receiving an actuating rod 16, and an outwardly directed circular flange 17, integral with the plunger which fits onto the flange 12A. The top of the closure is also provided with a circular V-shaped groove 18, which enables the flange 17 to be bent inward when the plunger is depressed. The plunger is covered with an aluminum cap 19 which is held in place by being crimped 20 under the flange 12A, said cap being provided with a center tear off seam 21 which is removed prior to the insertion of the activating rod.

The opposite end of the tubular syringe body is closed with an elastomeric plug cover 22 having an integral outwardly directed flange 23 which fits onto flange 12B. The cover has an outwardly directed raised center 24, and the side 25 of the plug cover fitting into the tubular unit is provided with substantially evenly spaced annular rings 26 which fit snugly; against the inner surface of the tube. The closure is held in place by an aluminum cap 27 which is crimped 28 under flange 12B. This cap has a center opening 29 for the insertion of the needle 30 into the narrowed thickness 31 of the closure, which opening is covered by a dust cap 32.

The holding assembly 33, for the needle is comprised of an elastomeric holder 34 having an opening 41 through which the needle is inserted and tightly held; the ends 35A and 35B of the needle projecting outside the unit. The unit is provided with a circular outer set of a plurality of spaced securing elements 36 projecting from and integral with the base 37 of the holder and a circular inner set of a plurality of shorter spaced securing elements 38 also projecting from and integral with the base of the holder, said circular inner and outer sets being substantially concentric. The outer securing elements have inwardly projecting barbs 39 and the inner securing elements have outwardly projecting barbs 40 whose functions are described below. Preferably, about 4 to 8 separate elements are present in each of the outer and inner sets. The portion of the needle which is to enter the patient is preferably protected with a cap 41 and the entire unit is held in a sealed sterile container.

The plunger or piston end of the preferred embodiment consists of an elastomeric plunger-closure of unique design. The portion of the plunger which is inserted into the syringe barrel or cylinder is similar to the plunger currently employed in pre-filled disposable syringes, but the embodiment of this invention also consists of a portion which is not inserted into the barrel. The preferred plunger or piston includes a flange which extends over the flange of the syringe barrel. This elastomeric plunger flange is integral with the main plunger body, but at the point where the flange joins the plunger proper, there is a thinning of the elastomer in the form of a V-shaped groove on the dorsal aspect, completely around the flange. When the protective aluminum seal is applied, as is commonly carried out in sealing serum vials, the resulting pressure on the rim of the closure-plunger will assure sterility integrity of the pre-filled syringe.

When the pre-filled syringe is readied for use, it is simply necessary to remove the seal which is a tear-off design commonly employed in sealing containers of injectible pharmaceuticals. Following the removal of the seal, the threaded seat of the plunger rod is exposed. The non-sterile plunger rod is seated appropriately by screwing into place into the threaded opening. When the needle end of the syringe has been properly readied, as will be described below, the plunger rod is depressed. The movement of the closure-plunger will cause the flange to fold back at the aforementioned groove or wedge shaped recess and serve merely as another ring of direct contact with the barrel wall. In this position, the flange will offer no greater resistance to the movement of the plunger than the other points of contact of the plunger with the barrel wall. It is well understood by one knowledgeable in the field of the aseptic filling process of pre-filled disposable syringes that a suitable lubricant must be employed to assure the smooth movement of the elastomeric plunger in this type of product. An appropriate lubricant is medical grade silicone.

The filling operation can be carried out following the placement of either closure; either the plunger end of the barrel or the needle end.

The assurance of sterility integrity at this needle end of the syringe is also guaranteed since a flange similar to the elastomeric flange described above is also present at the needle end. However, there are several differences in design of the closure and aluminum seal at the needle end of the pre-filled syringe. The aluminum seal and the under-rim crimp is identical at the periphery, but near the top center the seal is raised. To protect the top of the seal is a plastic tear off cap which is similar to those commonly in use. When the plastic cap is removed, it exposes the center of the elastomeric closure and the raised inside rim of the aluminum seal. Sealing equipment commercially available currently will have the capability of handling aluminum seals of this structure.

The purpose of the raised inner portion of the aluminum seal is described below.

The base of the needle assembly includes an inner and outer circular set (or rings) of split securing elements. The outer ring contains inward facing notched sections encompassing the entire outside ring which is interrupted by periodic slits to facilitate the appropriate movement of the notched sections in order to grasp the base of the aluminum cap or seal. The smaller ring is concentrically placed inside the ring described above, and the notches face outwardly. The inner ring is also split periodically as described previously. The purpose of this ring is to grasp or engage the top inner edge of the aluminum protective cap when the needle assembly is applied appropriately to the needle end of the syringe.

Simultaneously with the seating and engaging actions of the rings described above, the needle located in the center of the base of the needle assembly is placed over the center of the aluminum seal where the center of the elastomeric closure is exposed. The needle assembly is simply pressed into position finally placing the closure penetrating needle in a position where the needle pathway is now contiguous with the liquid present in the pre-filled syringe. It would be obvious to one skilled in the art that the syringe must be held with the needle pointing upwards, once the needle assembly has been fully locked into position, in order to prevent flow of liquid into the needle channel and to express air present in the syringe body prior to administering a dose into the recipient.

What is claimed is:

1. In a hypodermic syringe comprised of:
   (a) a syringe body adapted to be filled at either end, said syringe body being a tubular unit having circular outwardly directed flanges at each end,
   (b) piston closure means at one end of said syringe body, said closure means being adapted to receive an activating rod and having a circular outwardly directed flange engaging the outwardly directed flange of the tubular unit at the end of the tubular unit into which the piston closure means are inserted,
   (c) distal closure means at the opposite end of said tubular unit having a raised portion with a concave indentation centrally located on the raised portion, said closure means being adapted to receive a needle,
   (d) pierceable cover means over both closure means; the improvement which comprises holding means for a needle, said holding means comprising a base portion having a cylindrical opening in which the needle is held, a circular outer set of a plurality of spaced securing elements projecting inwardly from and integral with the base portion and a circular inner set of a plurality of shorter spaced securing elements projecting outwardly from and integral with the base portion, said outer and inner securing elements being arranged in concentric fashion, where the outer set of securing elements engages the flange at the distal end of said syringe body to fix the holding means to the syringe body, and the inner set of securing elements fits within the cover means disposed over the distal closure for engagement with said raised concave indentation and the inner surface of said cover means thereby securing said needle in a fixed position.

2. A hypodermic syringe according to claim 1 wherein the top surface of the plunger of the piston closure means is provided with a circular V-shaped groove where the flange joins the plunger.

* * * * *